United States Patent
Grumann et al.

(10) Patent No.: US 8,044,039 B2
(45) Date of Patent: Oct. 25, 2011

(54) QUETIAPINE HEMIFUMARATE PURIFICATION BY CRYSTALLIZATION

(75) Inventors: Arne Grumann, Kauniainen (FI); Soini Huhta, Espoo (FI); Petteri Rummakko, Espoo (FI); Viesturs Lusis, Riga (LV)

(73) Assignee: Fermion Oy, Espoo (FI)

( * ) Notice: Subject to any disclaimer, the term of this patent is extended or adjusted under 35 U.S.C. 154(b) by 699 days.

(21) Appl. No.: 12/083,975

(22) PCT Filed: Oct. 26, 2006

(86) PCT No.: PCT/FI2006/000344
§ 371 (c)(1), (2), (4) Date: Jul. 3, 2008

(87) PCT Pub. No.: WO2007/048870
PCT Pub. Date: May 3, 2007

(65) Prior Publication Data
US 2009/0156802 A1    Jun. 18, 2009

Related U.S. Application Data

(60) Provisional application No. 60/730,843, filed on Oct. 28, 2005.

(51) Int. Cl.
*A61K 31/554* (2006.01)
*C07D 281/16* (2006.01)
(52) U.S. Cl. .................. 514/211.13; 540/551
(58) Field of Classification Search ............. 514/211.13; 540/551
See application file for complete search history.

(56) References Cited

U.S. PATENT DOCUMENTS
2006/0063927 A1    3/2006    Etlin et al.

FOREIGN PATENT DOCUMENTS
EP     0 282 236 A1    9/1988
WO    WO-99/06381 A    2/1999

OTHER PUBLICATIONS

Ravikumar K. et al: "Quetiapine hemifumarate", Acta Crystallographica, Section E: Structure Reports Online, XX, XX, vol. E61, No. 10, Sep. 14, 2005, pp. 3245-3248.

*Primary Examiner* — Brenda Coleman
(74) *Attorney, Agent, or Firm* — Birch, Stewart, Kolasch & Birch, LLP

(57) ABSTRACT

The present invention relates to a process for preparing and purifying crystalline quetiapine hemifumarate, which comprises preparing crystalline quetiapine hemifumarate via a crystalline salt, which is not a salt of fumaric acid.

12 Claims, No Drawings

QUETIAPINE HEMIFUMARATE PURIFICATION BY CRYSTALLIZATION

This application is a National Stage entry of PCT International Application No. PCT/FI2006/000344 filed on Oct. 26, 2006, and claims priority under 35 U.S.C. §119(e) to Provisional Application No. 60/730,843 filed in the U.S. on Oct. 28, 2005, all of which are hereby expressly incorporated by reference into the present application.

FIELD OF THE INVENTION

The present invention relates to a novel process for the purification of quetiapine hemifumarate. More specifically, the purification comprises a crystallization process where quetiapine is crystallized consecutively as two different salts, the latter one being hemifumarate.

BACKGROUND OF THE INVENTION 11-(4-[2-(2-Hydroxyethoxy)ethyl]-1-piperazinyl]dibenzo[b,f]-1,4-thiazepine, is a well established drug substance known under the INN name quetiapine. It is used as its hemifumarate salt having the structure or formula (1)

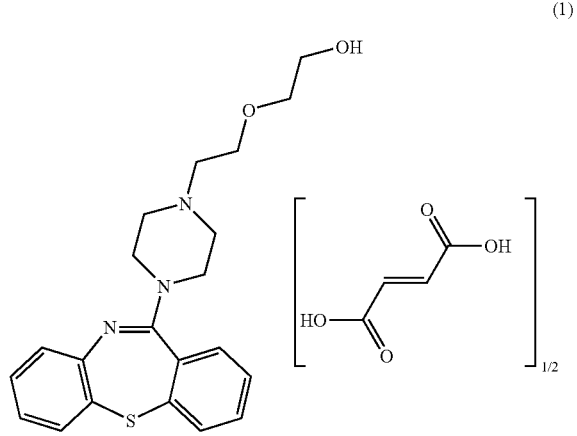

Quetiapine hemifumarate is a psychoactive compound that is an antagonist for multiple neurotransmitter receptors in the brain. Quetiapine hemifumarate is used as an antipsychotic or neuroleptic. Quetiapine hemifumarate is described, for example, in patent publication U.S. Pat. No. 4,879,288, which describes also the synthesis of quetiapine hemifumarate. Preparation of hemifumarate is described also e.g. in EP 0 282 236, and WO 01/55125. Different polymorphic forms of quetiapine hemifumarate and their preparation are described in WO 03/080065, WO 2004/076431 and WO 04/078735. The crystallization of quetiapine base and its use in the preparation of quetiapine hemifumarate is described in U.S. Pat. No. 6,372,734. There industrial methylated spirit is used as a solvent and it is said that crystalline fumarate salt is obtained in good purity and high yield without by-products of other salts. Anyhow, no information about the purity of the product is given.

SUMMARY OF THE INVENTION

Applicants have discovered that it is possible to improve the purity of quetiapine hemifumarate significantly if it is first crystallized as a different salt and then converted to the hemifumarate. The term different salt or first salt is used here to refer to any other salt of quetiapine than the salts of fumaric acid.

It is to be understood that the foregoing general description and the following detailed description are exemplary and explanatory only and are not restrictive of the invention as claimed.

DETAILED DESCRIPTION OF THE INVENTION

The present invention provides a novel possibility to improve the purity of quetiapine hemifumarate obtained by the crystallization process. As used herein and unless otherwise indicated, quetiapine hemifumarate refers to 11-(4-[2-(2-hydroxyethoxy)ethyl]-1-piperazinyl]dibenzo[b,f]-1,4-thiazepine fumarate (2:1) salt. The starting material, quetiapine base or quetiapine hemifumarate, for the crystallization can be made by any method described in the literature, e.g. as in U.S. Pat. No. 4,879,288 or EP 0 282 236. Thus the process of the invention can be used e.g. if crystalline quetiapine hemifumarate does not fulfil the specifications on impurities and further purification is needed.

Applicants have surprisingly discovered that crstallizng quetiapine first as some other salt and then converting it to the hemifumarate improves the purity of the product better than ordinary re-crystallization. An especially difficult impurity to remove by normal purification methods like re-crystallization is 2-(4-dibenzo[b,f]thiazepin-11-yl-piperazin-1-yl) ethanol. The term critical impurity is used herein to refer to this impurity. This impurity is formed when 2chloroethanol is present as an impurity in the 2-(2-chloroethoxy)ethanol or in2-hydroxyethoxyethylpiperazine used as raw material. According to IP.com publication no. IPCOM000041967D it has not been possible to remove this impurity by crystallization, but it has been necessary to remove 2-chloroethanol from the raw material by distillation. Now it has been surprisingly noticed that by the method of the present invention it is possible to reduce the amount of the critical impurity by up to 90% by varying the first salt and the solvent and depending on the amount of the impurity in the starting material. The amount of the critical impurity may be reduced using the herein described crystallization method even below quantitation limit. In comparison the effectivity of conventional recrystallization to remove the critical impurity in ethanol is typically only around 10%. The salts which can be used as first crystallization salts are e.g. tosylate or hydrohalic acid salts, preferably hydrochloride is used as the first salt.

Thus, the present invention relates to a novel process for the preparation of crystalline quetiapine hemifumarate which comprises crystallizing first quetiapine as e.g. as hydrohalic acid salt and converting it to the hemifumarate.

In another aspect, the present invention provides a process for crystallizing quetiapine hemifumarate comprising
a) dissolving quetiapine base in a solvent;
b) converting quetiapine to the first quetiapine salt;
c) cooling the mixture to precipitate the first quetiapine salt;
d) isolating the first quetiapine salt; and
e) converting the first quetiapine salt to quetiapine hemifumarate salt.

In another aspect, the present invention provides a process for purifying quetiapine hemifumarate comprising
a) dissolving quetiapine hemifumarate in a solvent;
b) optionally liberating quetiapine base from quetiapine hemifumarate
c) converting quetiapine to the first quetiapine salt;
d) cooling the mixture to precipitate the first quetiapine salt;
e) isolating the first quetiapine salt; and f) converting the first quetiapine salt to quetiapine hemifumarate.

Suitable solvents in the first crystallization step include but are not limited to, methanol ethanol n-propanol, iso-propanol ethylene glycol, mixtures of alcohol with water or acetone depending on the salt to be formed, e.g. if hydrochloride is made, the preferred solvent is ethanol, butanol, isopropanol or acetone, and if tosylate is made, the preferred solvent is acetone.

The typical crystallization process of the first salt includes the steps of heating a solution of quetiapine base, which may be obtained from the hemifumarate using a suitable base, in a crystallization solvent with the acid used for the the salt formation for a time sufficient to dissolve the quetiapine base; crystallization using a typical cooling profile with cooling rate from 1° C./h to 20° C./h; and isolating the quetiapine first salt and washing and drying it. The crystallization may optionally be initiated with the aid of seed crystals.

The ratio of quetiapine to treating solvent is not critical. Typically 1-10 times of volume of solvent per gram of quetiapine base is used.

Similarly, the heating time is not critical. The skilled artisan will know to optimize the time depending on, among other things, the quetiapine used as a starting material, the reagent for the salt formation and the ratio of quetiapine to treating solvent.

The temperature of the solution is decreased during the crystallization. Usually a linear cooling system is used, but also other systems are possible. When the typical crystallization cooling profile is used the temperature is decreased to about 20° C. to 0° C. In particular, the temperature is decreased gradually over a period of time. Optionally also seeding crystals may be used.

Crystallization time is not critical but can vary from about 1 to about 20 hours, with 3 to 10 hours being typical. The skilled artisan will know to adjust the crystallization time according to the relative amounts of quetiapine, salt forming reagent, crystallization solvent and the equipment used.

Following treatment, the first crystalline quetiapine salt is isolated by suitable means known to the skilled artisan and routiner alike, for example, filtration or centrifugation. The isolated solid quetiapine first salt can be dried, or used as such to make fumarate salt or be re-crystallized if necessary.

The first quetiapine salt is transferred to the hemifumarate in a similar way. The base is liberated from the first salt using a suitable inorganic or organic base, e.g. NaOH, KOH, $Na_2CO_3$ or $K_2CO_3$ can be used. The hemifumarate can be made as described in prior art using fumaric acid and isolated by methods known in the art.

The invention will be further clarified by the following nonlimiting examples, which are intended to be purely exemplary of the invention. The quetiapine fumarate or quetiapine base used in examples can be made by processes known in the art, e.g. as described in U.S. Pat. No. 4,879,288 or EP 0 282 236.

EXAMPLES

Preparation of Quetiapine Hydrochloride from Quetiapine Fumarate

Example 1

Crude quetiapine fumarate (HPLC purity 99,89 a-%, critical impurity 0,08 a-%) 10 g was suspended to ethanol (20 ml) and heated at 60° C. 15 w-% EtOH-HCl solution (8 ml ) was added to the stirred mixture at 60° C. The mixture was stirred until all solid material was dissolved and stirred at 60° C. for 30 min. The reaction mixture was cooled to 0° C., cooling rate 10° C./h and stirred 1 h at 0° C. Quetiapine hydrochloride crystals were collected by filtration and washed once with cold ethanol. The product 7, 95 g was obtained as white crystals having HPLC purity of 99,98%, critical impurity was not detected.

Example 2

Crude quetiapine fumarate (10 g, HPLC purity 99,70 a-%, critical impurity 0,08 a-%) was suspended to isopropanol (30 ml) and heated at 70° C. 30 w-% HCl solution (2,5 ml ) was added to stirred reaction mixture at 70° C. The mixture was stirred until all solid material was dissolved and stirred at 70° C. for 30 min. The reaction mixture was cooled to 0° C., cooling rate 10° C./h and stirred 1 h at 0° C. Quetiapine hydrochloride crystals were collected by filtration and washed once with cold isopropanol to obtain 8,28 g white crystals having HPLC purity of 99,89%, critical impurity was not detected.

Preparation of Quetiapine Hydrochloride from Quetiapine Free Base

Example 3

Quetiapine base 8 g (HPLC-purity 96,87 a-% and critical impurity 0,16 a-%) was dissolved to ethanol 16 ml and heated to reflux. Ethanol-HCl solution 15 w-% 5 g was added to hot ethanol quetiapine mixture and allowed to cool to 0° C. Cooling rate was 10° C./h and the mixture was stirred for 1 h at 0° C. The crstals were filtered of and dried. The yield of quetiapine hydrochloride was 6,0 g and HPLC-purity 99,65%. Critical impurity was not detected.

Conversion of Quetiapine Hydrochloride to Quetiapine Fumarate

Example 4

Quetiapine hydrochloride (6 g) was added to a mixture of water (10 ml) and methanol (10 ml). The mixture was stirred for ca. 10 min to dissolve solid material. Toluene 30 ml was added and the pH of the solution was adjusted to 13-14 by addition of 50% NaOH solution. The mixture was heated to 40-50° C. and stirred for 10 min. The toluene phase was separated and washed once with water (10 ml). The toluene solution was evaporated under reduced pressure. The remaining residue was dissolved to 80% ethanol (24 ml) and fumaric acid (0,85 g) was added to the solution. The mixture was heated to reflux for 10 min and cooled to 0° C. The solid material was filtered to give pure white crystals of quetiapine fumarate 4,92 g.

Conversion of Quetiapine Free Base to Quetiapine Tosylate

Example 5

Solution of toluenesulfonic acid monohydrate (1.13 g) in acetone (10 ml) was added to quetiapine base (prepared from 2.61 g of hemifumarate HPLC purity 99,40 and the amount of critical impurity was 0,13%) dissolved in toluene (155 ml) under stirring. The formed oily mixture was slightly warmed to dissolve the oil and left at room temperature for 4 h and then at 0° C. overnight. The precipitate was filtered off to obtain Q.TsOH salt in 3.05 g amount (HPLC purity 99,88 and critical impurity 0,01%.

Examples of the decrease in the amount of the critical impurity obtained by the method of the invention are presented in table 1.

TABLE 1

The amount of 2-(4-dibenzo[b,f]thiazepin-11-yl-piperazin-1-yl) ethanol as an impurity in quetiapine hemifumarate before and after re-crystallization via first quetiapine salt.

| Crystallization | Critical impurity* before crystallization | Solvent | Critical impurity* after crystallization |
|---|---|---|---|
| re-crystallization | 0.08% | Ethanol | 0.07% |
| via HCl | 0.11% | Ethanol | 0.02% |
| via HCl | 0.20% | IPA | 0.11% |
| via HCl | 0.13% | IPA | 0.04% |
| via HCl | 0.14% | Ethanol | 0.04% |
| via HCl– | 0.13% | Acetone | 0.04% |
| via HCl | 0.13% | n-Butanol | 0.03% |
| via benzoate | 0.13% | Acetone | 0.08% |
| via tosylate | 0.13% | Acetone | 0.01% |

*2-(4-dibenzo[b,f]thiazepin-11-yl-piperazin-1-yl) ethanol

The invention claimed is:

1. A process for preparing crystalline quetiapine hemifumarate comprising the steps: a) crystallizing quetiapine first salt from a suitable solvent and; b) converting the first salt to quetiapine hemifumarate.

2. A process for crystallizing quetiapine hemifumarate comprising a) dissolving quetiapine base in a solvent; b) converting quetiapine to the first quetiapine salt; c) cooling the mixture to precipitate the first quetiapine salt; d) isolating the first quetiapine salt; and e) converting the first quetiapine salt to quetiapine hemifumarate.

3. A process according to claim 1 or 2 wherein the first quetiapine salt is quetiapine hydrochloride.

4. A process according to claim 1 or 2, wherein the first quetiapine salt is quetiapine tosylate.

5. A process of claim 1 or 2 wherein the first quetiapine salt is quetiapine hydrochloride and the crystallization solvent is ethanol, butanol, isopropanol or acetone.

6. A process of claim 1 or 2 wherein the first quetiapine salt is quetiapine tosylate and the crystallization solvent is acetone.

7. A process for purifying quetiapine hemifumarate comprising a) dissolving crude quetiapine hemifumarate in a solvent; b) optionally liberating quetiapine base from quetiapine hemifumarate; c) converting quetiapine to the first quetiapine salt; d) cooling the mixture to precipitate the first quetiapine salt; e) isolating the first quetiapine salt; and f) converting the first quetiapine salt to quetiapine hemifumarate.

8. A process according to claim 7 wherein the first quetiapine salt is quetiapine hydrochloride.

9. A process according to claim 7 wherein the first quetiapine salt is quetiapine tosylate.

10. A process of claim 7 wherein the first quetiapine salt is quetiapine hydrochloride and the crystallization solvent is ethanol, butanol, isopropanol or acetone.

11. A process of claim 7 wherein the first quetiapine salt is quetiapine tosylate and the crystallization solvent is acetone.

12. A method of making a pharmaceutical composition comprising mixing quetiapine hemifumarate made by claim 1 or 2 with a pharmaceutically acceptable carrier.

* * * * *